(12) United States Patent
Tsubota et al.

(10) Patent No.: US 12,290,393 B2
(45) Date of Patent: May 6, 2025

(54) CONTROL DEVICE, IMAGE ACQUISITION DEVICE, CONTROL METHOD, AND CONTROL PROGRAM

(71) Applicant: FUJIFILM CORPORATION, Tokyo (JP)

(72) Inventors: Keiji Tsubota, Kanagawa (JP); Hidetoshi Takayama, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 293 days.

(21) Appl. No.: 18/188,465

(22) Filed: Mar. 23, 2023

(65) Prior Publication Data

US 2023/0309946 A1 Oct. 5, 2023

(30) Foreign Application Priority Data

Mar. 29, 2022 (JP) ................. 2022-054507

(51) Int. Cl.
*A61B 6/04* (2006.01)
*A61B 6/00* (2006.01)
*A61B 6/50* (2024.01)
*A61B 8/08* (2006.01)

(52) U.S. Cl.
CPC .............. *A61B 6/54* (2013.01); *A61B 6/0414* (2013.01); *A61B 6/502* (2013.01); *A61B 8/0825* (2013.01)

(58) Field of Classification Search
CPC ... A61B 6/0414; A61B 6/0407; A61B 6/0421; A61B 6/0487; A61B 6/6502; A61B 6/547; A61B 8/403; A61B 8/40
See application file for complete search history.

(56) References Cited

U.S. PATENT DOCUMENTS

2005/0089205 A1   4/2005   Kapur et al.

FOREIGN PATENT DOCUMENTS

EP    3744257 A1 * 12/2020 ........... A61B 6/0414
JP    2005-125080 A    5/2005

* cited by examiner

*Primary Examiner* — Don K Wong
(74) *Attorney, Agent, or Firm* — SOLARIS Intellectual Property Group, PLLC (57) ABSTRACT

A control device comprising at least one processor, wherein the at least one processor is configured to: acquire type information indicating a type of a compression member attached to an image acquisition device that captures a radiation image by irradiating a breast in a compressed state between an imaging table and the compression member with radiation; and set an upper limit value of a compression force applied to the breast by the compression member based on the type information.

18 Claims, 7 Drawing Sheets

| IDENTIFICATION INFORMATION | TYPE INFORMATION | | |
|---|---|---|---|
| | MATERIAL | SIZE (WIDTH x DEPTH x HEIGHT) (mm) | SHAPE |
| T01 | PC | 300 × 240 × 70 | FOR CC/MLO |
| T02 | PC | 240 × 180 × 40 | FOR SMALL BREAST CC/MLO |
| T03 | PMP | 300 × 240 × 70 | FOR CC/MLO |
| T04 | PMP | 240 × 180 × 40 | FOR SMALL BREAST CC/MLO |
| T05 | PC | 90 × 90 × 40 | FOR SPOT IMAGING |
| T05 | PC | 200 × 80 × 70 | FOR AXILLA |
| T06 | PC | 240 × 180 × 40 | FOR BIOPSY |
| ⋮ | ⋮ | ⋮ | ⋮ |

FIG. 8

| No. | TYPE OF COMPRESSION MEMBER | UPPER LIMIT VALUE (N) OF COMPRESSION FORCE |
|---|---|---|
| 0 | STANDARD (CASE NOT CORRESPONDING TO THE BELOW) | 200 |
| 1 | MATERIAL IS PMP | 150 |
| 2 | WIDTH OR DEPTH IS 250 mm OR MORE | 190 |
| 3 | SHAPE IS FOR BIOPSY | 150 |
| ⋮ | ⋮ | ⋮ |

USAGE INFORMATION

| THE NUMBER OF TIMES OF COMPRESSION | USAGE DATE | COMPRESSION FORCE (N) | COMPRESSION TIME (SEC) |
|---|---|---|---|
| 1 | 03/01/2022 | 80 | 23 |
| 2 | 03/01/2022 | 150 | 18 |
| 3 | 03/02/2022 | 120 | 25 |
| ⋮ | ⋮ | ⋮ | ⋮ |

FIG. 11

| No. | TYPE OF COMPRESSION MEMBER | CONDITION | | |
|---|---|---|---|---|
| | | THE NUMBER OF TIMES OF COMPRESSION | LOAD AMOUNT | ELAPSED TIME |
| 0 | STANDARD (CASE NOT CORRESPONDING TO THE BELOW) | 500,000 | $5 \times 10^8$ | 6 YEARS |
| 1 | MATERIAL IS PMP | 300,000 | $2 \times 10^8$ | 4 YEARS |
| 2 | WIDTH OR DEPTH IS 250 mm OR MORE | 400,000 | $4 \times 10^8$ | 6 YEARS |
| 3 | SHAPE IS FOR BIOPSY | 200,000 | $1 \times 10^8$ | 3 YEARS |
| ⋮ | ⋮ | ⋮ | ⋮ | ⋮ |

FIG. 12

CONTROL DEVICE, IMAGE ACQUISITION DEVICE, CONTROL METHOD, AND CONTROL PROGRAM

CROSS-REFERENCE TO RELATED APPLICATIONS

This application claims priority from Japanese Application No. 2022-054507, filed on Mar. 29, 2022, the entire disclosure of which is incorporated herein by reference.

BACKGROUND

Technical Field

The present disclosure relates to a control device, an image acquisition device, a control method, and a control program.

Related Art

In the related art, an image acquisition device that captures a radiation image of a breast is known. In addition, from the viewpoint of improving a detection accuracy of breast cancer, a device capable of acquiring an ultrasound image of a breast in addition to a radiation image has been proposed. For example, JP2005-125080A discloses acquiring an X-ray image of a breast, determining coordinates of an ROI that can be observed on an X-ray image and includes an abnormal portion, and scanning an object with an ultrasound imaging system by using the coordinates of the ROI. In addition, in a case of acquiring an X-ray image and an ultrasound image, it is disclosed that the breast is put into a compressed state by a compression paddle.

By the way, in an image acquisition device that acquires a radiation image and/or an ultrasound image of a breast, it is desired that a compression member for putting the breast into a compressed state can be attached and detached. For example, it is desired that the compression member can be replaced with a compression member having a suitable material, size, and shape according to a shape such as a size of the breast, a tissue composition such as a fat mass and a mammary gland mass, and a purpose of imaging.

On the other hand, if the materials, the sizes, and the shapes of the compression member are different, strengths thereof are also different. In particular, a compression member having a relatively low strength may deteriorate more quickly than a compression member having a relatively high strength. Therefore, there is a demand for a technique capable of appropriately suppressing deterioration for each compression member.

SUMMARY

The present disclosure provides a control device, an image acquisition device, a control method, and a control program capable of suppressing deterioration of the compression member.

A first aspect of the present disclosure is a control device comprising at least one processor, in which the processor is configured to: acquire type information indicating a type of a compression member attached to an image acquisition device that captures a radiation image by irradiating a breast in a compressed state between an imaging table and the compression member with radiation; and set an upper limit value of a compression force applied to the breast by the compression member based on the type information.

In the first aspect, the type information may indicate at least one of a material, a size, or a shape of the compression member.

In the first aspect, the type information may indicate at least the material of the compression member.

In the first aspect, the processor may be configured to: in a case where the type information indicates that the compression member is of a type having a relatively high strength, set a relatively high value as the upper limit value; and in a case where the type information indicates that the compression member is of a type having a relatively low strength, set a relatively low value as the upper limit value.

In the first aspect, the processor may be configured to, in a case where the type information indicates a material containing polymethylpentene, set a value relatively lower than those of other materials as the upper limit value.

In the first aspect, the processor may be configured to acquire, for each compression member, a log including usage information indicating at least one of the compression force, a compression time, or the number of times of compression applied to the breast by the compression member, or an elapsed time from a point in time at which the compression member is first used.

In the first aspect, the processor may be configured to, in a case where the usage information satisfies a condition predetermined for each type of the compression member, issue a notification.

In the first aspect, the processor may be configured to: derive a load amount of the compression member based on the usage information; and in a case where the load amount satisfies a condition predetermined for each type of the compression member, issue a notification.

In the first aspect, the processor may be configured to, in a case where the usage information satisfies a condition predetermined for each type of the compression member, set a relatively low value as the upper limit value.

In the first aspect, the processor may be configured to: derive a load amount of the compression member based on the usage information; and in a case where the load amount satisfies a condition predetermined for each type of the compression member, set a relatively low value as the upper limit value.

In the first aspect, the processor may be configured to decrease the compression force after completion of capturing the radiation image to less than the compression force before completion of capturing the radiation image, based on the type information.

In the first aspect, the processor may be configured to, in a case where the type information indicates a material containing polymethylpentene, decrease the compression force after completion of capturing the radiation image to less than the compression force before completion of capturing the radiation image.

In the first aspect, the processor may be configured to: acquire a movement amount of the compression member in a compression direction with respect to the breast; monitor deformation of the compression member based on the movement amount; and in a case where the deformation of the compression member is detected, execute at least one of notification or stopping of compression by the compression member.

In the first aspect, the processor may be configured to, in a case where the movement amount becomes larger than a predetermined threshold value, detect that the compression member is deformed.

A second aspect of the present disclosure is an image acquisition device comprising: the control device according to the first aspect; a radiation source; a radiation detector; an imaging table disposed between the radiation source and the radiation detector; and a compression member that compresses a breast between the compression member and the imaging table.

In the second aspect described above, the image acquisition device may further comprise an ultrasound probe disposed between the radiation source and the compression member.

A third aspect of the present disclosure is a control method comprising: acquiring type information indicating a type of a compression member attached to an image acquisition device that captures a radiation image by irradiating a breast in a compressed state between an imaging table and the compression member with radiation; and setting an upper limit value of a compression force applied to the breast by the compression member based on the type information.

A fourth aspect of the present disclosure is a control program for causing a computer to execute a process comprising: acquiring type information indicating a type of a compression member attached to an image acquisition device that captures a radiation image by irradiating a breast in a compressed state between an imaging table and the compression member with radiation; and setting an upper limit value of a compression force applied to the breast by the compression member based on the type information.

According to the above-described aspects, the control device, the image acquisition device, the control method, and the control program of the present disclosure can suppress deterioration of the compression member.

DETAILED DESCRIPTION

First Embodiment

Hereinafter, embodiments of the present disclosure will be described with reference to the drawings.

Figure 1:
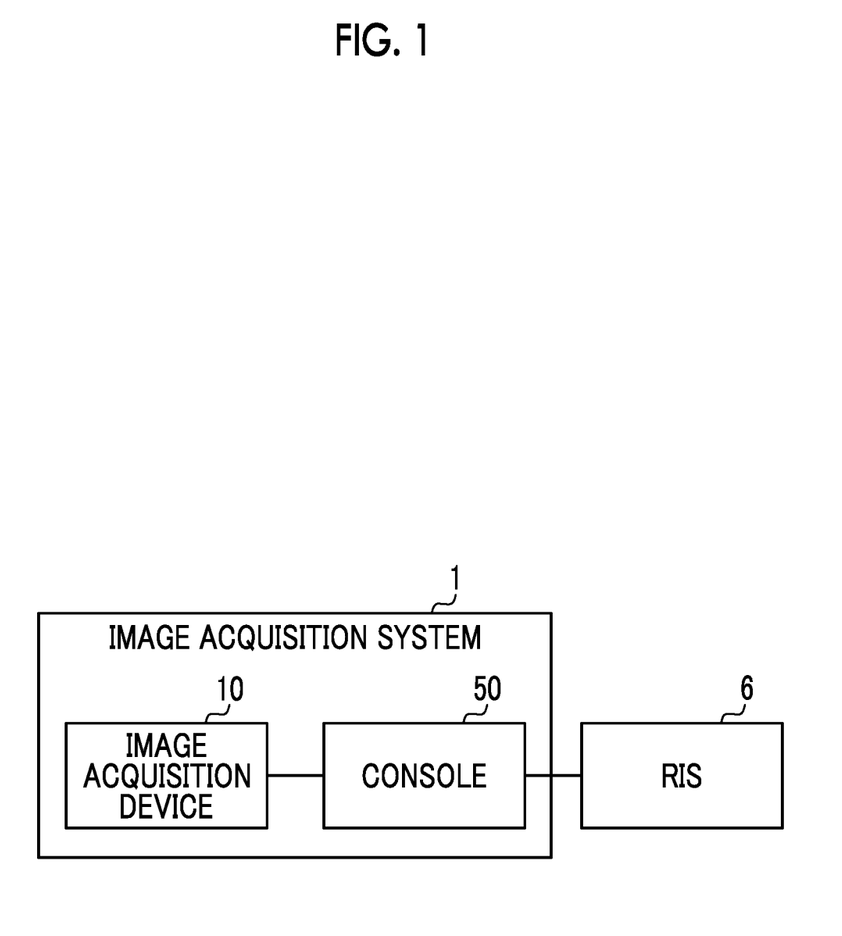
FIG. 1 is a view showing an example of a schematic configuration of an image acquisition system.

First, a configuration of an image acquisition system 1 to which an image acquisition device 10 of the present disclosure is applied will be described with reference to FIG. 1. FIG. 1 is a view showing a schematic configuration of the image acquisition system 1. As shown in FIG. 1, the image acquisition system 1 includes the image acquisition device 10 and a console 50. The image acquisition device 10 and the console 50, and the console 50 and an external radiology information system (RIS) 6 are configured to be connectable to each other via a wired or wireless network. The console 50 is an example of a control device of the present disclosure.

In the image acquisition system 1, the console 50 acquires an imaging order or the like from the RIS 6 and controls the image acquisition device 10 in response to the imaging order, an instruction from the user, and the like. The image acquisition device 10 captures a radiation image by irradiating a breast in a compressed state between an imaging table 16 and a compression member 40 with radiation R. In addition, the image acquisition device 10 acquires an ultrasound image of the breast in the compressed state via the compression member 40.

Figure 2:
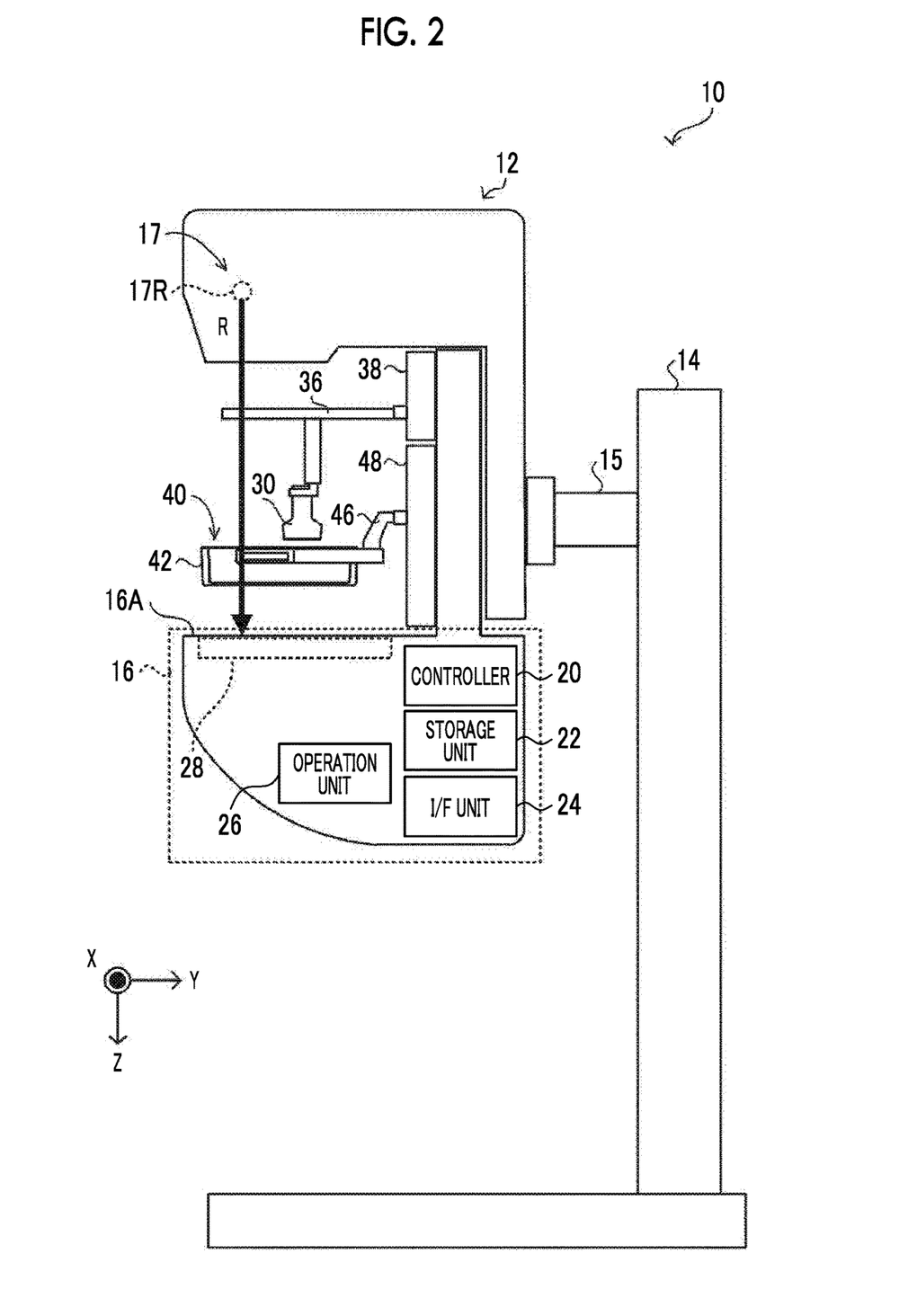
FIG. 2 is a side view showing an example of an appearance of the image acquisition device.

Next, a schematic configuration of the image acquisition device 10 will be described with reference to FIG. 2. FIG. 2 is a side view showing an example of an appearance of the image acquisition device 10 and is a view in a case where the image acquisition device 10 is viewed from a right side of a subject. As shown in FIG. 2, the image acquisition device 10 comprises a radiation source 17R, a radiation detector 28, an imaging table 16 disposed between the radiation source 17R and the radiation detector 28, the compression member 40 that compresses the breast between the compression member 40 and the imaging table 16, and an ultrasound probe 30. In the image acquisition device 10, a user such as a doctor or a technician positions the breast of the subject on an imaging surface 16A of the imaging table 16.

The image acquisition device 10 comprises an arm part 12, a base 14, and a shaft part 15. The arm part 12 is movably held in a vertical direction (Z direction) by the base 14. The shaft part 15 connects the arm part 12 to the base 14. The arm part 12 is rotatable relative to the base 14 with the shaft part 15 as a rotation axis. Further, the arm part 12 may be rotatable relative to the base 14 with the shaft part 15 as the rotation axis separately between an upper portion comprising the radiation emitting unit 17 and a lower portion comprising the imaging table 16.

The arm part 12 includes the radiation emitting unit 17 and the imaging table 16. The radiation emitting unit 17 comprises the radiation source 17R and is configured to change an irradiation field of radiation (for example, X-rays) emitted from the radiation source 17R. For example, the change of the irradiation field may be performed by the user operating an operation unit 26 or may be performed by a controller 20 according to a type of the attached compression member 40.

The imaging table 16 comprises the controller 20, a storage unit 22, an interface (I/F) unit 24, the operation unit 26, and the radiation detector 28. The controller 20 controls an overall operation of the image acquisition device 10 according to the control of the console 50. The controller 20 includes a central processing unit (CPU), a read only memory (ROM), a random access memory (RAM), and the like (not shown). The ROM stores in advance various programs including a program executed by the CPU for performing control regarding acquisition of the radiation image and the ultrasound image. The RAM temporarily stores various types of data.

The storage unit 22 stores data of the radiation image and the ultrasound image, and other various types of information. The storage unit 22 is realized by, for example, a storage medium such as a hard disk drive (HDD), a solid state drive (SSD), and a flash memory.

The I/F unit 24 communicates various types of information with the console 50 by wired communication or wireless communication. Specifically, the I/F unit 24 receives information regarding the control of the image acquisition device 10 from the console 50. In addition, the I/F unit 24 transmits the data of the radiation image and the ultrasound image to the console 50.

The operation unit 26 is a part provided on the imaging table 16 or the like and operable by the user with a hand, a foot, or the like, and is, for example, a switch, a button, a touch panel, or the like.

The radiation detector 28 is disposed inside the imaging table 16, detects the radiation R transmitted through the breast and the imaging table 16, generates the radiation image based on the detected radiation R, and outputs image data representing the generated radiation image. The type of the radiation detector 28 is not particularly limited and may be, for example, an indirect conversion type radiation detector that converts the radiation R into light and converts the converted light into a charge, or a direct conversion type radiation detector that directly converts the radiation R into a charge.

Further, a probe unit 38 and a compression unit 48 are connected to the arm part 12. A support part 36 that attachably and detachably supports the ultrasound probe 30 is attached to the probe unit 38. The support part 36 (ultrasound probe 30) is moved in a vertical direction and a horizontal direction (X direction, Y direction, and Z direction) by a driving unit (not shown) provided in the probe unit 38. The support part 36 is preferably formed of a material that transmits the radiation R.

The ultrasound probe 30 is used for obtaining the ultrasound image of the breast in a compressed state by the compression member 40, is disposed between the radiation source 17R and the compression member 40, irradiates the breast with ultrasonic waves via the compression member 40, and receives reflected waves from the breast. Further, the probe unit 38 includes a converter (not shown) that converts the reflected waves from the breast received by the ultrasound probe 30 into the ultrasound image, and the ultrasound image is obtained by the converter.

Specifically, the ultrasound probe 30 comprises an ultrasound transducer array. The ultrasound transducer array has a configuration in which a plurality of ultrasound transducers are arranged one-dimensionally or two-dimensionally. The ultrasound transducer may be constituted, for example, by forming electrodes at both ends of a piezoelectric body such as a piezoelectric ceramic represented by lead zirconate titanate (PZT), a piezoelectric single crystal represented by lead magnesium niobate-lead titanate (PMN-PT), and a polymeric piezoelectric element represented by polyvinylidene difluoride (PVDF). Further, for example, the ultrasound transducer may be a capacitive micro-machined ultrasound transducer (CMUT).

In addition, a plurality of different types of ultrasound probes 30 may be interchangeably attached to the image acquisition device 10. Specifically, depending on a physique of the subject (for example, a size of the breast), a tissue composition of the breast (for example, a fat mass and a mammary gland mass), a type of imaging (for example, magnified imaging and spot imaging), and the like, the ultrasound probes 30 having different performances and dimensions may be attached. For example, a linear probe having a center frequency of about 7.5 MHz (for superficial use, etc.), a convex probe having a center frequency of about 3.5 MHz (for abdomen, etc.), a sector probe having a center frequency of about 2.5 MHz (for heart, etc.), and the like may be used.

A support part 46 that supports the compression member 40 is attachably and detachably mounted to the compression unit 48. The support part 46 (compression member 40) is moved in the vertical direction (Z direction) by a driving unit (not shown) provided in the compression unit 48.

Figure 3:
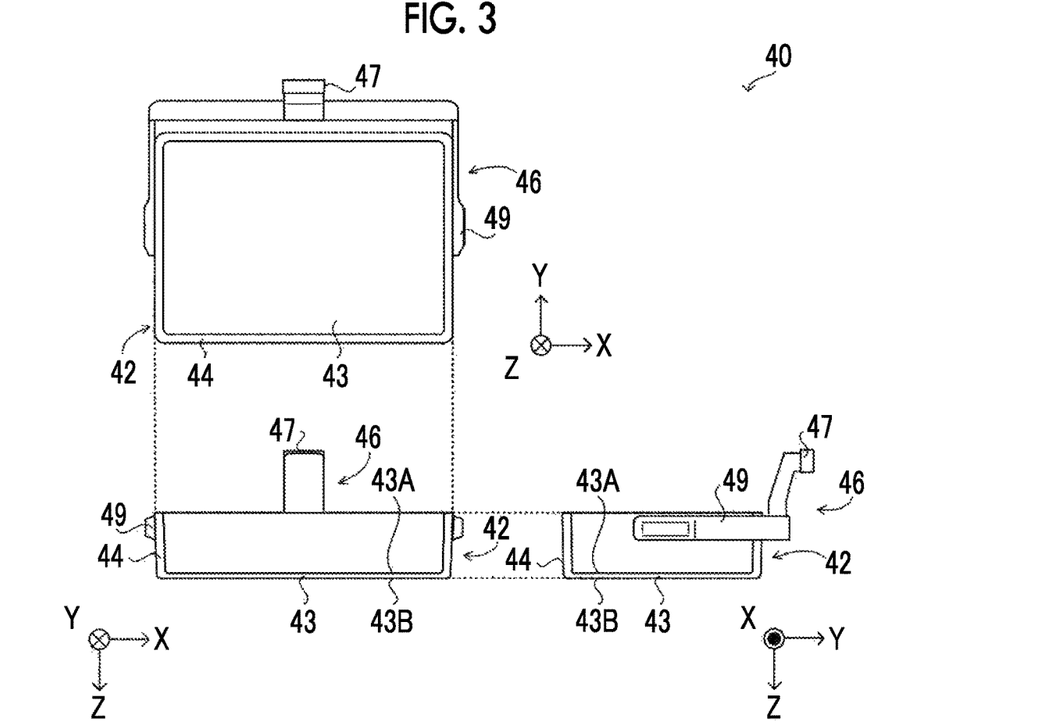
FIG. 3 is a three-view diagram showing an example of a schematic configuration of a compression member.

The compression member 40 is disposed between the radiation source 17R and the imaging table 16 and sandwiches the breast between the compression member 40 and the imaging table 16 to bring the breast into a compressed state. FIG. 3 shows a three-view diagram of an example of the compression member 40. The three-view diagram of FIG. 3 includes a top view of the compression member 40 as viewed from above (the radiation emitting unit 17 side), a side view thereof as viewed from the subject side, and a side view thereof as viewed from the right side of the subject. As shown in FIG. 3, the compression member 40 includes a compression part 42 and the support part 46.

The support part 46 includes an attachment portion 47 and an arm 49. The attachment portion 47 attaches the compression member 40 to the image acquisition device 10, specifically, the driving unit of the compression unit 48. The arm 49 supports the compression part 42.

The compression part 42 includes a bottom portion 43 formed to be substantially flat and surrounded by a wall portion 44 having a substantially uniform height and has a cross-sectional shape formed in a recessed shape. The compression part 42 is preferably formed of an optically transparent or translucent material in order to perform positioning and confirmation of a compressed state in compression of the breast. In addition, the compression part 42 is preferably formed of a material excellent in transmittance of the radiation R and ultrasonic waves. Further, the compression part 42 is preferably formed of, for example, a material excellent in strength such as drop strength and compression strength.

As such a material, for example, a resin such as polymethylpentene (PMP), polycarbonate (PC), acryl, polypropylene (PP), and polyethylene terephthalate (PET) can be used. In particular, in the polymethylpentene, an acoustic impedance, which affects transmittance and reflectivity of ultrasonic waves, is close to that of a human body (breast) as compared with other materials, and a proportion of noise on the ultrasound image can be reduced. Therefore, the polymethylpentene is suitable as the material for the compression part 42.

In addition, a plurality of different types of compression members 40 may be interchangeably attached to the image acquisition device 10. Specifically, depending on a physique of the subject (for example, a size of the breast), a tissue composition of the breast (for example, a fat mass and a mammary gland mass), a type of imaging (for example, magnified imaging and spot imaging), and the like, the compression members 40 having different materials, sizes, and shapes may be attached. For example, a compression member according to the size of the breast, a compression member for axillary imaging, a compression member for magnified imaging, and a compression member for so-called spot imaging that captures a radiation image of only a region where a lesion exists, and the like may be used. That is, the compression member 40 is not limited to the one that compresses the entire breast, and may be smaller than the breast to compress a part of the breast.

Figure 4:
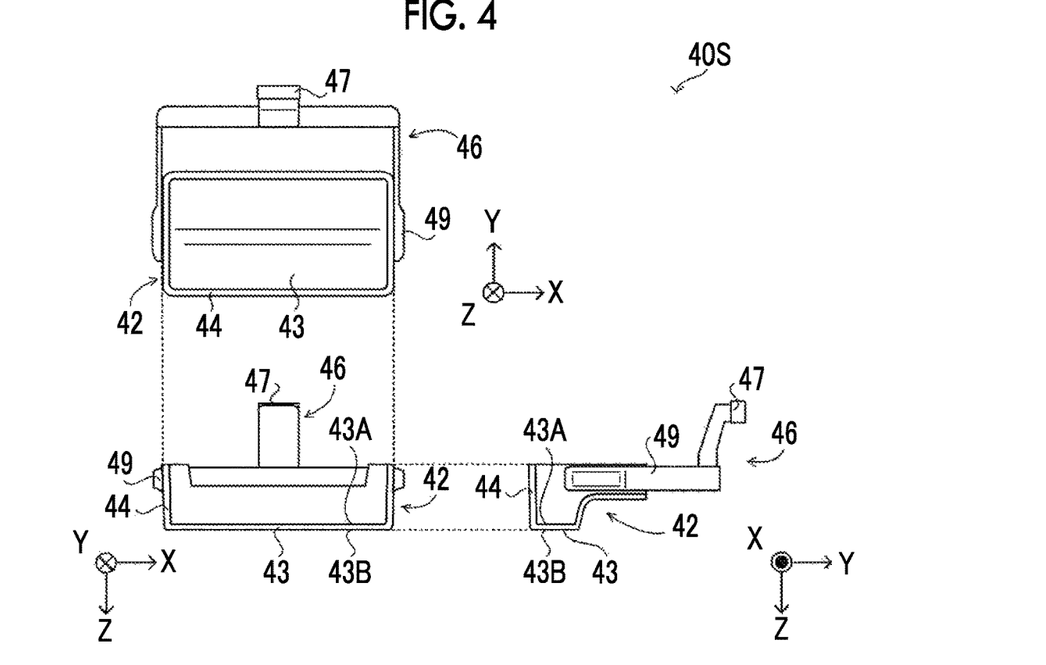
FIG. 4 is a three-view diagram showing an example of a schematic configuration of a compression member.

FIG. 4 shows a three-view diagram of the compression member 40S for a small breast as an example of another form different from the compression member 40 of FIG. 3. The three-view diagram of FIG. 4 includes a top view of the compression member 40S as viewed from above (the radiation emitting unit 17 side), a side view thereof as viewed from the subject side, and a side view thereof as viewed from the right side of the subject. The compression member 40S includes a compression part 42 and a support part 46, similarly to the compression member 40 in FIG. 3. In the compression member 40S, the bottom portion 43 is not flat, and the attachment portion 47 side is higher than a chest wall side (a side away from the attachment portion 47). In addition, a height of a wall portion 44 is not uniform, and a height of a part of the chest wall side is lower than a height of other parts. Due to such a shape, the compression member 40S can easily perform positioning and compression even in a small breast.

In this way, in the image acquisition device 10, at least one of the compression member 40 for putting the breast into a compressed state or the ultrasound probe 30 for acquiring the ultrasound image can be attachable and detachable. In this case, the image acquisition device 10 may detect the type of the compression member 40 and the ultrasound probe 30 that are attached.

For example, the attachment portion 47 of the compression member 40 may be provided with a plurality of pins having different arrangements for each type of the compression member 40 as identification information, and the identification information may be read by a sensor (for example, a photointerruptor) capable of detecting the arrangement of the pins provided in the compression unit 48. Further, for example, a marker (for example, a bar code, a two-dimensional code, or the like) corresponding to the type of the compression member 40 may be provided at any position of the compression member 40 as identification information, and the identification information may be read by a sensor (for example, a charge coupled device (CCD) sensor or the like) capable of detecting the marker.

Further, for example, a radio frequency identification (RFID) tag having identification information corresponding to the type of the compression member 40 may be provided at any position of the compression member 40 and the identification information may be read by an RFID reader capable of reading the RFID tag. Further, for example, a weight of each type of the compression member 40 and the identification information may be stored in the storage unit 22 in advance in association with each other, a weight of the attached compression member 40 may be measured by a sensor capable of detecting the weight, and the identification information (type of the compression member 40) may be specified based on a measured value.

Similarly, for the ultrasound probe 30, the type of the attached ultrasound probe 30 may be identified according to, for example, a pin, a marker, an RFID tag, a weight, or the like.

In addition, the image acquisition device 10 may detect a compression force applied to the breast by the compression member 40. For example, in a case where the compression member 40 compresses the breast, a reaction force equal to the compression force is applied to the driving unit of the compression member 40. Utilizing this, a strain gauge (for example, a load cell or the like) for detecting the reaction force applied to the driving unit may be provided in the compression unit 48, and the reaction force detected by the strain gauge may be detected as the compression force. Further, for example, the compression force may be detected by using a semiconductor pressure sensor, a capacitive pressure sensor, and the like. Further, for example, various sensors for detecting the compression force may be provided on the compression member 40 side instead of the compression unit 48 side.

In addition, a gel-like or liquid medium having ultrasound transmittance may be applied to an upper surface 43A and/or a breast contact surface 43B of the bottom portion 43 of the compression member 40. As such a medium, for example, a known jelly for ultrasonic examination, which has an acoustic impedance close to an acoustic impedance of a human body (breast), can be applied. That is, the image acquisition device 10 may acquire an ultrasound image of the breast compressed by the compression member 40 in a state of being coated with the gel-like or liquid medium having ultrasound transmittance via the compression member 40. In this case, it is possible to suppress entry of air into an interface between an ultrasound radiation surface of the ultrasound probe 30 and the upper surface 43A and/or an interface between the contact surface 43B and the breast, and to reduce a difference in acoustic impedance at each interface so that the proportion of noise on the ultrasound image can be reduced.

In addition, a method of imaging the breast by the image acquisition device 10 is not particularly limited. For example, cranio-caudal (CC) imaging, medio-lateral oblique (MLO) imaging, magnified imaging and spot imaging for imaging a part of the breast, and the like may be performed. The CC imaging is a method of imaging the breast in a compressed state by sandwiching the breast between the imaging table 16 and the compression member 40 in the vertical direction (Z direction). The MLO imaging is a method of imaging the breast in a compressed state including an axillary portion by sandwiching the breast between the imaging table 16 and the compression member 40 in a tilted state in which a rotation angle of the arm part 12 with respect to the base 14 is 45 degrees or more and less than 90 degrees.

Further, for example, the image acquisition device 10 may perform tomosynthesis imaging. In the tomosynthesis imaging, the radiation R is emitted from each of a plurality of irradiation positions having different irradiation angles toward the breast by the radiation source 17R, and a plurality of radiation images of the breast are captured. That is, in the tomosynthesis imaging, the imaging is performed by changing a rotation angle of the radiation emitting unit 17 with respect to the base 14 while keeping angles of the imaging table 16, the compression member 40, the breast, and the like.

In addition, in the image acquisition device 10, the breast of the subject may be positioned not only in a state in which the subject is standing up (standing state), but also in a state in which the subject is sitting on a chair, a wheelchair, or the like (sitting state).

The console 50 sets an upper limit value of the compression force applied to the breast by the compression member 40 according to the type of the compression member 40 attached to the image acquisition device 10. In addition, the console 50 controls the image acquisition device 10 such that the radiation image is acquired in response to an imaging order acquired from the RIS 6, an instruction from the user, and the like. In addition, the console 50 controls a position of the ultrasound probe 30 such that the ultrasound image can be acquired in accordance with a position of a region of interest included in the radiation image captured in the image acquisition device 10. Hereinafter, the console 50 will be described.

Figure 5:
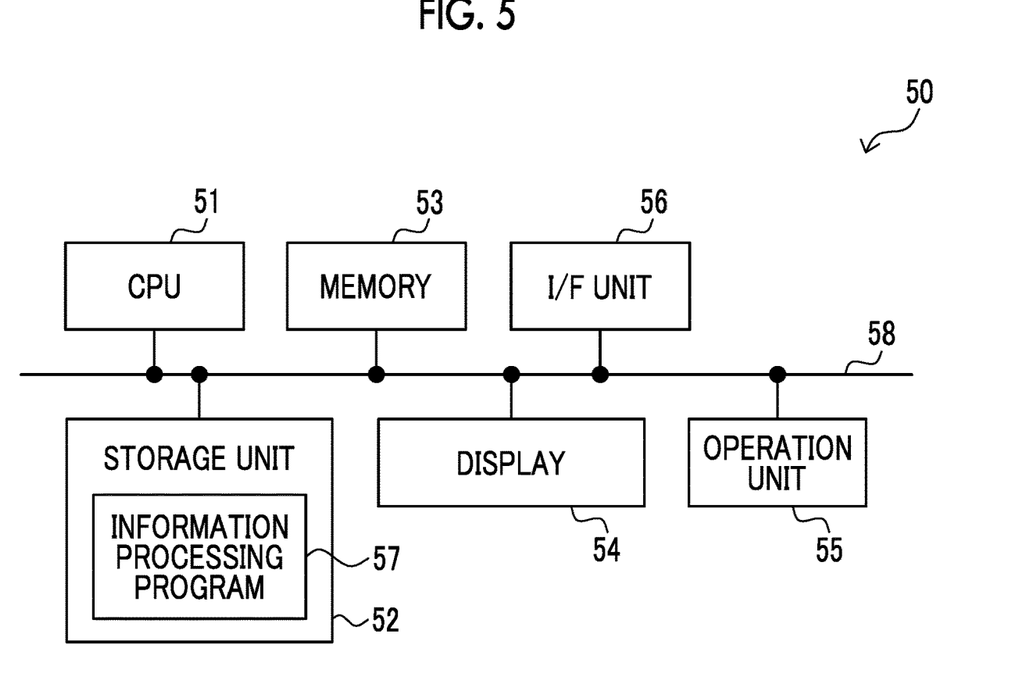
FIG. 5 is a block diagram showing an example of a hardware configuration of a console.

An example of a hardware configuration of the console 50 will be described with reference to FIG. 5. As shown in FIG. 5, the console 50 includes a CPU 51, a non-volatile storage unit 52, and a memory 53 as a temporary storage area. In addition, the console 50 includes a display 54 such as a liquid crystal display, an operation unit 55 such as a touch panel, a keyboard, and a mouse, and an I/F unit 56. The I/F unit 56 performs wired or wireless communication with the image acquisition device 10, the RIS 6, and other external devices. The CPU 51, the storage unit 52, the memory 53, the display 54, the operation unit 55, and the I/F unit 56 are connected to each other via a bus 58 such as a system bus and a control bus such that various types of information can be exchanged.

The storage unit 52 is realized by, for example, a storage medium such as an HDD, an SSD, and a flash memory. The storage unit 52 stores an information processing program 57 in the console 50. The CPU 51 reads the information processing program 57 from the storage unit 52, develops the information processing program 57 into the memory 53, and executes the developed information processing program 57. As the console 50, for example, a personal computer, a server computer, a smartphone, a tablet terminal, a wearable terminal, or the like can be appropriately applied.

In addition, the storage unit 52 stores image data of the radiation image and the ultrasound image acquired by the image acquisition device 10, various types of other information, and the like. The image data of the radiation image and the ultrasound image may be stored in association with at least one of an imaging order or imaging information. The imaging information may include, for example, at least one of subject information and an imaging item that are included in the imaging order, photographer information indicating a photographer (for example, a user such as a doctor or a technician) who performed the imaging, or date and time information indicating date and time when the imaging was performed.

Figure 6:
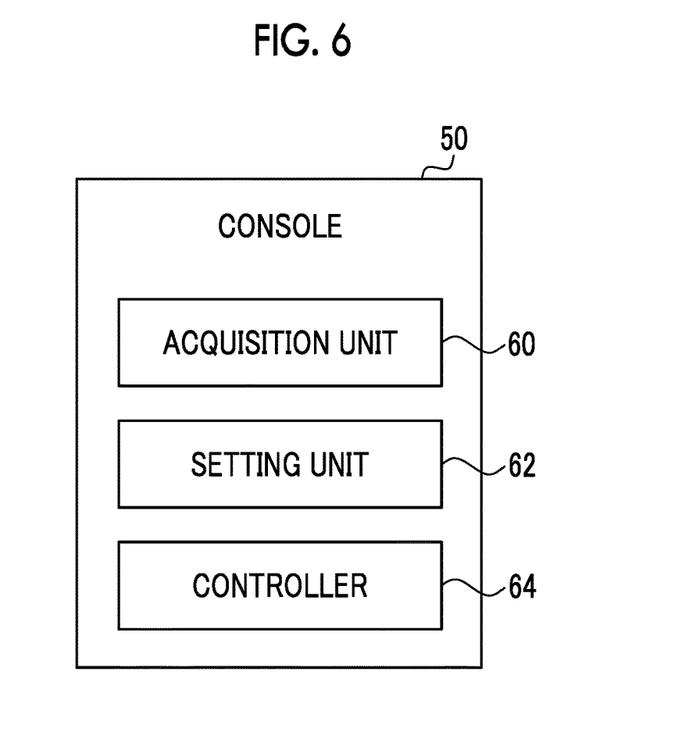
FIG. 6 is a block diagram showing an example of a functional configuration of the console.

An example of a functional configuration of the console 50 will be described with reference to FIG. 6. As shown in FIG. 6, the console 50 includes an acquisition unit 60, a setting unit 62, and a controller 64. By executing the information processing program 57 by the CPU 51, the CPU 51 functions as the acquisition unit 60, the setting unit 62, and the controller 64.

Setting of Upper Limit Value of Compression Force

The acquisition unit 60 acquires type information indicating the type of the compression member 40 attached to the image acquisition device 10. The type information is information indicating at least one of a material, a size, or a shape of the compression member 40 attached to the image acquisition device 10. In particular, it is preferable that the type information indicates at least the material of the compression member 40 attached to the image acquisition device 10.

Figure 7:
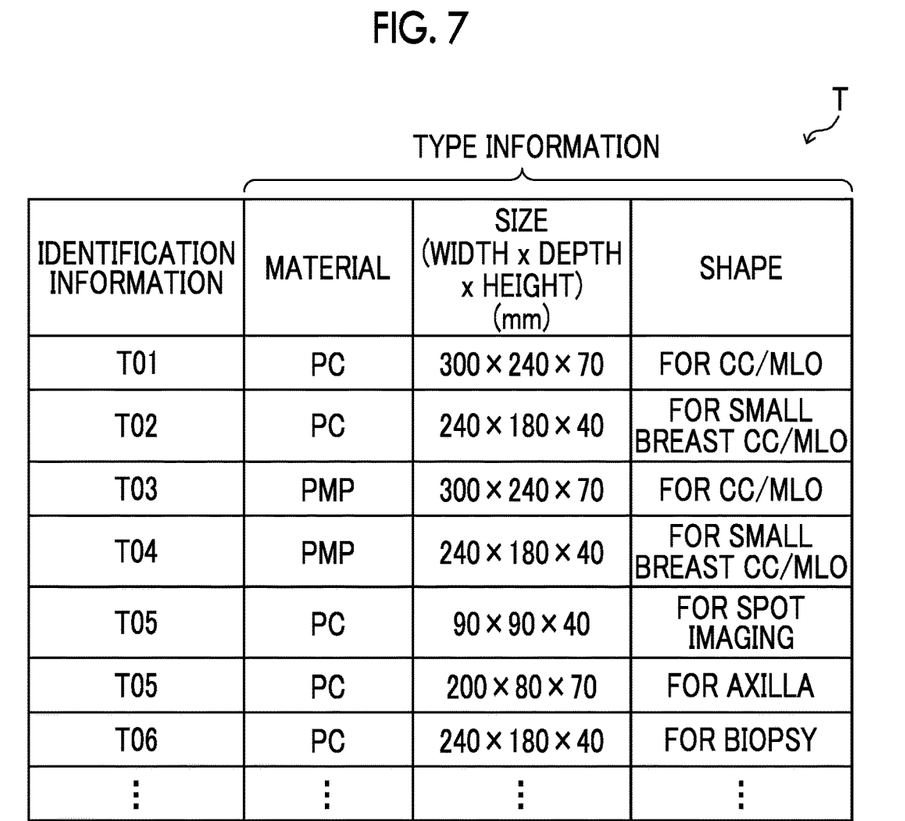
FIG. 7 is a diagram showing an example of type information of the compression member.

FIG. 7 shows an example of the type information of the compression member 40. FIG. 7 shows a table T in which identification information, a material, a size including a width (X direction), a depth (Y direction), and a height (Z direction), and a shape of the compression member 40 are associated with each other. "For CC/MLO" shown in the column of the shape means, for example, a compression member having a flat plate-shaped bottom portion 43 as shown in FIG. 3. "For small breast CC/MLO" means, for example, a compression member having a shape in which the bottom portion 43 is not flat as shown in FIG. 4 and which makes it easy to pull out the hand of the user who performs positioning. "For spot imaging" and "For axilla" mean compression members having sizes suitable for spot imaging and imaging of an axillary portion, respectively. "For biopsy" means, for example, a compression member in which a hole through which a needle for collecting cells and/or tissues of the breast passes is provided in the bottom portion 43.

For example, the acquisition unit 60 may acquire the identification information indicating the type of the compression member 40 detected by the image acquisition device 10 and collate the identification information with the table T to specify the type information of the compression member 40 attached to the image acquisition device 10. The table T may be stored in advance in, for example, the storage unit 52.

The setting unit 62 sets an upper limit value of the compression force applied to the breast by the compression member 40 based on the type information acquired by the acquisition unit 60. Specifically, the setting unit 62 sets a relatively low value as the upper limit value of the compression force in a case where the type information indicates that the compression member 40 is of a type having a relatively low strength. In other words, in a case where the type information indicates that the compression member 40 is of a type having a relatively high strength, the setting unit 62 sets a relatively high value as the upper limit value of the compression force. The "strength" means, for example, a mechanical strength evaluated by bending strength, tensile yield stress (yield point stress), or the like.

For example, it is considered that the strength of the compression member 40 varies depending on the material. As described above, as the material of the compression member 40, resins such as polymethylpentene (PMP) and polycarbonate (PC) can be used, and PMP is particularly suitable from the viewpoint of an acoustic impedance. However, it is known that the strength of PMP is low as compared with other materials such as PC. For example, the bending strength of PC is about 91 to 94 MPa (megapascal), whereas that of PMP is about 25 to 40 MPa. Further, for example, the tensile yield stress of PC is about 63 to 69 MPa and that of PMP is about 25 to 32 MPa. Therefore, in a case where the type information acquired by the acquisition unit 60 indicates a material containing polymethylpentene (PMP), the setting unit 62 may set a relatively lower value than that of other materials (for example, PC) as the upper limit value of the compression force.

Further, for example, it is considered that the strength of the compression member 40 varies depending on the size and the shape. For example, between the compression member 40 of FIG. 3 and the compression member 40S of FIG. 4, it can be said that the compression member 40 of FIG. 3 in which the bottom portion 43 is larger is more likely to be deformed and has a lower strength. Therefore, in a case where the type information acquired by the acquisition unit 60 indicates a size and a shape in which the strength is relatively small, the setting unit 62 may set a relatively low value as the upper limit value of the compression force than a case where the type information indicates other sizes and shapes.

Figure 8:
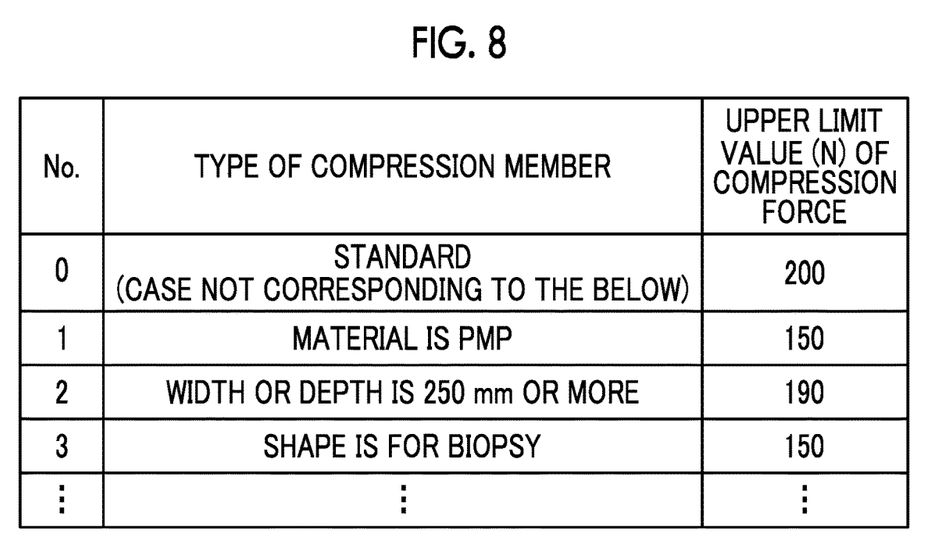
FIG. 8 is a diagram showing an example of an upper limit value of a compression force set based on the type information.

FIG. 8 shows an example of the upper limit value of the compression force set based on the type information. As shown in FIG. 8, the setting unit 62 may set a predetermined upper limit value of the compression force for each piece of the type information (that is, at least one of a material, a size, or a shape of the compression member 40). For example, in a case where a plurality of the upper limit values are set based on the type information, such as in a case where the type information satisfies No. 1 and No. 2 in FIG. 8 at the same time, the setting unit 62 may set the upper limit value of the compression force to the lowest value (150 N (Newton)). The upper limit value of the compression force predetermined for each piece of the type information may be stored in advance in, for example, the storage unit 52.

Acquisition of Radiation Image

The acquisition unit 60 acquires the imaging order from the RIS 6. The imaging order includes, for example, subject information such as a name, gender, and date of birth of the subject to be imaged, an imaging item for performing the imaging, and the like. The imaging item is, for example, various types of imaging such as CC imaging, MLO imaging, magnified imaging, spot imaging, and tomosynthesis imaging which are designated for each of left and right breasts.

The controller 64 causes the display 54 to display an instruction to a user such as a doctor or a technician to perform positioning and compression of the breast according to the imaging order acquired by the acquisition unit 60. In addition, the controller 64 controls the image acquisition device 10 such that the compression force exceeding the upper limit value set by the setting unit 62 is not applied. In a case where the positioning and compression of the breast by the user are completed, the controller 64 gives an instruction to the image acquisition device 10 to capture the radiation image according to the imaging order.

Acquisition of Ultrasound Image

After the radiation image is captured by the image acquisition device 10 in response to an imaging instruction from the controller 64, the acquisition unit 60 acquires the radiation image. Specifically, the acquisition unit 60 may acquire the radiation image stored in the storage unit 22 of the image acquisition device 10 via the I/F unit 56, may acquire the radiation image stored in the storage unit 52, or may acquire the radiation image stored in the external device.

The controller 64 extracts a region of interest included in the radiation image acquired by the acquisition unit 60. The region of interest is, for example, a region of abnormal shadow that appears on the radiation image due to a lesion such as a calcification or a tumor. The region of interest may be extracted using, for example, a known computer aided detection/diagnosis (CAD) technique, or a region designated by the user via the operation unit 55 may be extracted as the region of interest.

As a method of extracting the region of interest using the CAD technique, for example, a method using a learning model such as a convolutional neural network (CNN) may be applied. For example, the controller 64 may extract the region of interest from the radiation image by using a learning model that is trained such that the radiation image is input and the region of interest included in the radiation image is extracted and output.

The controller 64 controls the position of the ultrasound probe 30 in the image acquisition device 10 such that the region of interest extracted from the radiation image is reflected in the ultrasound image. Specifically, the controller 64 specifies a position on the compression member 40 corresponding to the region of interest, and gives an instruction to the image acquisition device 10 to move the ultrasound probe 30 to the specified position on the compression member 40.

Figure 9:
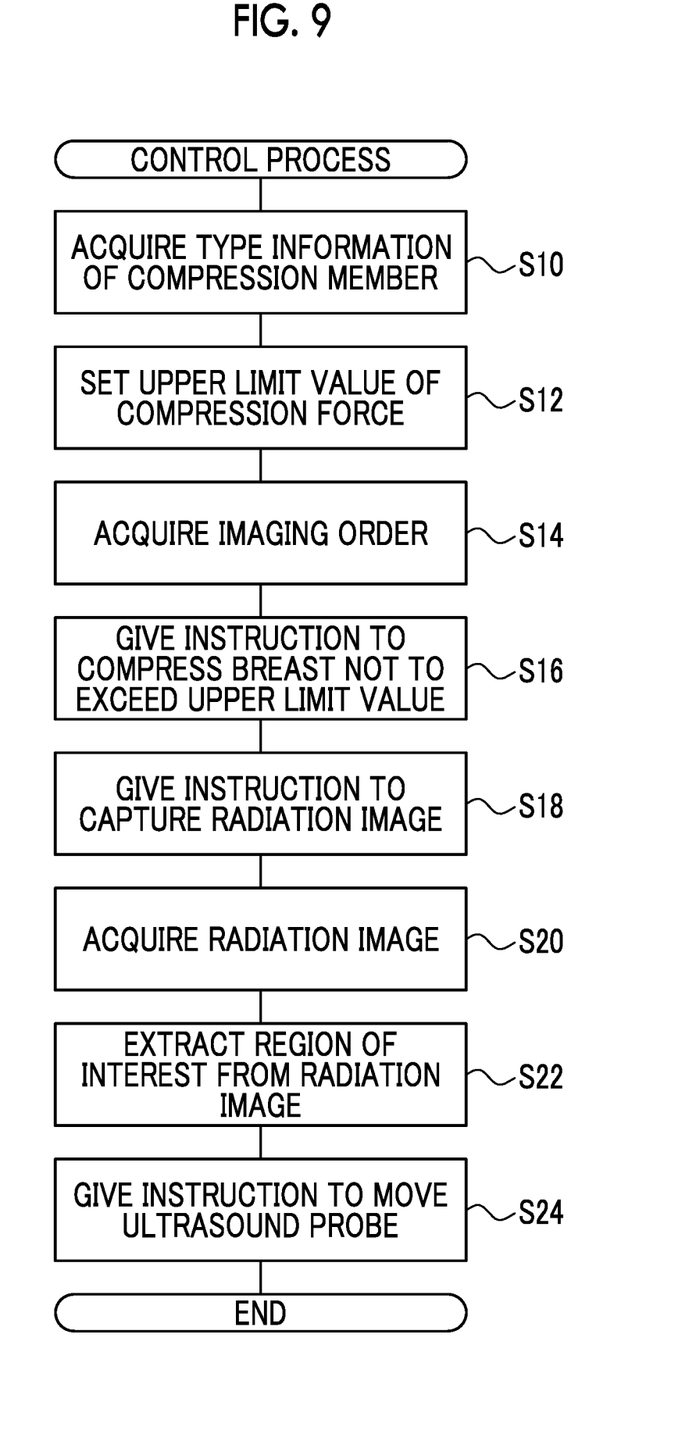
FIG. 9 is a flowchart showing an example of a control process.

Next, an operation of the console 50 according to the present embodiment will be described with reference to FIG. 9. In the console 50, the CPU 51 executes the information processing program 57 to execute a control process shown in FIG. 9. The control process is executed, for example, in a case where the user gives an instruction to start execution via the operation unit 55.

In step S10, the acquisition unit 60 acquires the type information indicating the type of the compression member 40 attached to the image acquisition device 10. In step S12, the setting unit 62 sets the upper limit value of the compression force applied to the breast by the compression member 40 based on the type information acquired in step S10. In step S14, the acquisition unit 60 acquires the imaging order from the RIS 6. In step S16, the controller 64 displays an instruction on the display 54 to perform the positioning and compression of the breast according to the imaging order acquired in step S14 and controls the image acquisition device 10 such that the compression force exceeding the upper limit value set in step S12 is not applied.

In step S18, the controller 64 gives an instruction to the image acquisition device 10 to capture the radiation image according to the imaging order acquired in step S14. In step S20, the acquisition unit 60 acquires the radiation image captured by the image acquisition device 10 in response to the instruction in step S18. In step S22, the controller 64 extracts the region of interest included in the radiation image acquired in step S20. In step S24, the controller 64 gives an instruction to the image acquisition device 10 to move the ultrasound probe 30 to a position where the region of interest extracted in step S22 is reflected in the ultrasound image and ends the control process.

As described above, the console 50 according to one aspect of the present disclosure comprises at least one processor, in which the processor is configured to acquire type information indicating a type of a compression member 40 attached to an image acquisition device 10 that captures a radiation image by irradiating a breast in a compressed state between an imaging table 16 and the compression member 40 with radiation R, and set an upper limit value of a compression force applied to the breast by the compression member 40 based on the type information.

That is, with the console 50 according to the present embodiment, the upper limit value of the compression force can be appropriately set according to the type of the compression member 40 attached to the image acquisition device 10. For example, even in a case where the compression member 40 is replaced with a compression member 40 having a suitable material, size, and shape according to a shape such as a size of the breast, a tissue composition such as a fat mass and a mammary gland mass, and a purpose of imaging, the upper limit value of the compression force can be appropriately controlled according to a strength of each compression member 40. Therefore, regardless of which type of compression member 40 is attached to the image acquisition device 10, strong compression that deforms the compression member 40 is not performed, and deterioration of the compression member 40 can be appropriately suppressed.

In addition, in the first embodiment, as shown in FIG. 8, it has been described that a relatively low value is set as the upper limit value of the compression force in a case where it is determined that the compression member 40 has a relatively low strength based on at least one of a material, a size, or a shape of the compression member 40, but the present disclosure is not limited thereto. For example, the upper limit value of the compression force may be predetermined for each piece of the type information (that is, for each piece of the identification information) of the compression member 40 according to the strength thereof, and may be stored in the storage unit 52 in addition to the table T in FIG. 7. In this case, the upper limit value of the compression force can be set more appropriately for each type (material, size, and shape) of the compression member 40.

Second Embodiment

It is considered that in a case where types of the compression member 40, that is, strengths of the compression member 40 are different, rates of deterioration of the compression member 40 due to repeated compression are also different. Therefore, the console 50 according to the second embodiment records a usage status for each compression member 40 and manages the compression member 40 with different standards according to the type of the compression member 40. Hereinafter, functions of the console 50 according to the second embodiment will be described, but a part of the description that overlaps with the first embodiment will be omitted.

Figure 10:
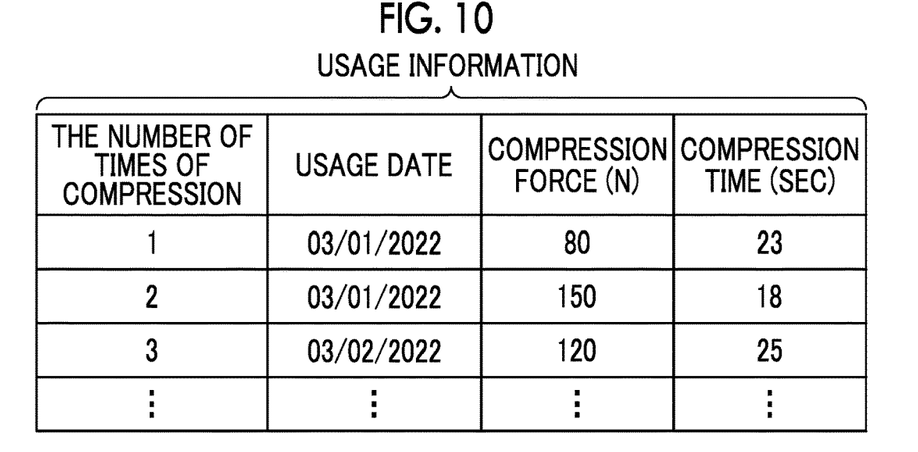
FIG. 10 is a diagram showing an example of usage information.

The acquisition unit 60 acquires, for each compression member 40, a log including usage information indicating at least one of a compression force, a compression time, or the number of times of compression applied to the breast by the compression member 40 attached to the image acquisition device 10, or an elapsed time from a point in time at which the compression member 40 is first used. The compression time is a time during which the compression member 40 applies a compression force equal to or greater than a predetermined threshold value to the breast. FIG. 10 shows an example of a log including usage information about one compression member 40.

For example, the image acquisition device 10 may detect the identification information unique to each of the attached compression members 40 and record the identification information, and the compression force and the compression time detected by a sensor in the storage unit 22 in association with each other. In addition, after the acquisition of the radiation image and/or the ultrasound image by the image acquisition device 10 is completed, the acquisition unit 60 may acquire the identification information, the compression force, and the compression time recorded in the storage unit 22 of the image acquisition device 10, create a log of usage information for each piece of the identification information, and store the log in the storage unit 52. In addition, similarly to the identification information for each type of the compression member 40 described above, the image acquisition device 10 may detect the identification information unique to each of the attached compression members 40 according to, for example, a pin, a marker, an RFID tag, a weight, or the like.

The controller 64 performs control of performing notification in a case where the usage information acquired by the acquisition unit 60 satisfies conditions predetermined for each type of the compression member 40. Specifically, the controller 64 may issue a warning and a notification prompting the replacement of the compression member 40 in a case where it is determined that the compression member 40 may have deteriorated based on the usage information. For example, the controller 64 may display notification content on the display 54 of the console 50. Further, for example, the controller 64 may perform notification using lighting and/or extinguishing by a light emitting diode (LED) provided in the console 50 or the image acquisition device 10. Further, for example, the controller 64 may perform notification by emitting a sound from a speaker provided in the console 50 or the image acquisition device 10.

Figure 11:
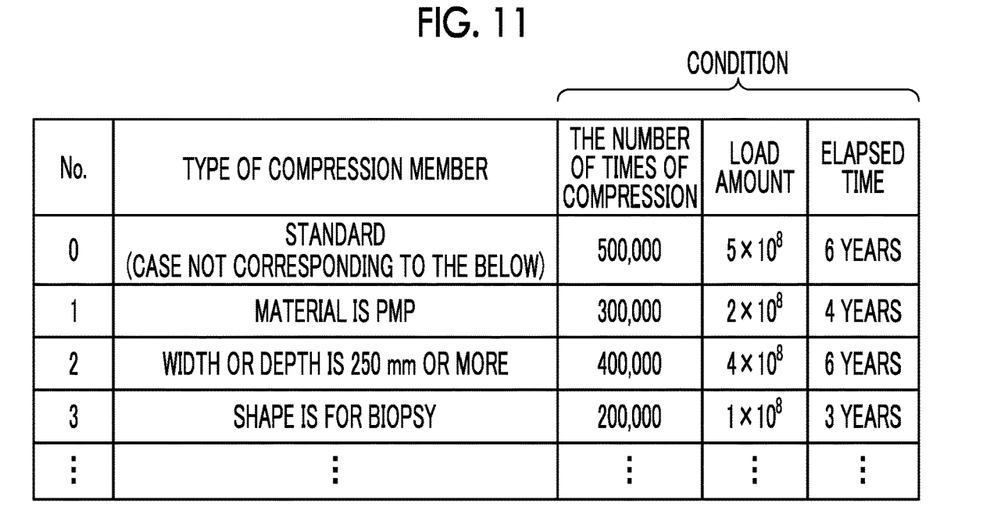
FIG. 11 is a diagram showing an example of a condition in which the usage information is used.

FIG. 11 shows an example of predetermined conditions for each type of the compression member 40. As shown in FIG. 11, the predetermined conditions are, for example, threshold values related to the number of times of compression, a load amount applied to the compression member 40, an elapsed time from a point in time at which the compression member 40 is first used, and the like. For example, the deterioration of the compression member 40 progresses as the compression is repeated. Therefore, in a case where the number of times of compression exceeds a predetermined threshold value, the controller 64 may perform notification.

Further, for example, the deterioration of the compression member 40 progresses faster as the load amount applied to the compression member 40 increases. Therefore, the controller 64 may derive the load amount of the compression member 40 based on the usage information and perform notification in a case where the derived load amount satisfies a predetermined condition for each type of the compression member 40. Specifically, the deterioration of the compression member 40 progresses faster as the compression force is stronger and the compression time is longer. Therefore, in a case where the compression force is P, the compression time is T, and a predetermined constant is A at each time at which compression by the compression member 40 is performed, the controller 64 may derive an integrated value represented by the following equation as a load amount L.

$$L=\Sigma(P \times T \times A)$$

Further, for example, the compression member 40 deteriorates over time due to light, moisture, temperature change, or the like. Further, from the viewpoint of hygiene, it is desirable that the compression member 40 is periodically replaced. Therefore, in a case where an elapsed time from a point in time at which the compression member 40 is first used exceeds a predetermined threshold value, the controller 64 may perform notification. The elapsed time can be specified, for example, based on a period from a first use date recorded in the log to the present time.

The controller 64 may control whether or not to perform notification by appropriately combining conditions regarding the number of times of compression, the load amount, and the elapsed time. For example, the notification may be performed at a point in time at which any one of a plurality of the conditions is satisfied, or the notification may be performed at a point in time at which all of the conditions are satisfied.

For the compression member 40 that may have progressed in deterioration, the progress of deterioration may be delayed by setting the upper limit value of the compression force applied to the breast by the compression member 40 to be lower. Therefore, in a case where the usage information acquired by the acquisition unit 60 satisfies a condition predetermined for each type of the compression member 40, the controller 64 may perform control to set a relatively low value as the upper limit value of the compression force applied to the breast by the compression member 40. Similarly, the controller 64 may set a relatively low value as the upper limit value of the compression force in a case where the load amount derived based on the usage information satisfies the condition predetermined for each type of the compression member 40.

For example, the upper limit value of the compression force of the compression member 40 of which the material is PMP is 150 N in an initial state (state in which the number of times of compression is 0) (see FIG. 8). In a case where the usage information regarding the compression member 40 satisfies the condition of No. 1 in FIG. 11, the controller 64 may reset the upper limit value of the compression force to a relatively low value (for example, 130 N). In addition, for example, the controller 64 may provide a condition stepwise, and in a case where a condition in which deterioration is considered to have progressed further (for example, the number of times of compression is more than 400,000) is satisfied, set the upper limit value of the compression force to a lower value (for example, 120 N).

As described above, according to the console 50 according to the present embodiment, a degree of deterioration can be appropriately managed in consideration of the usage status and the type of the compression member 40 attached to the image acquisition device 10. Therefore, it is possible to suppress deformation of the compression member 40 that may occur due to the deterioration of the compression member 40.

Third Embodiment

In capturing the radiation image, in order to reduce an exposure dose, improve an image quality, and suppress a body movement, it is required to compress the breast with a strong compression force during irradiation with the radiation R. On the other hand, acquiring the ultrasound image may take longer time than capturing the radiation image due to work such as scanning the ultrasound probe 30 while looking at the image and looking for a lesion. During this period, it is not preferable to continue to compress the breast with the same strong compression force as in a case of capturing the radiation image, because the deterioration of the compression member 40 progresses to cause a burden on the subject. Therefore, the console 50 according to the third embodiment changes the compression force applied to the breast by the compression member 40 at each stage of the capture of the radiation image and the acquisition of the ultrasound image. Hereinafter, functions of the console 50 according to the third embodiment will be described, but a part of the description that overlaps with the first and second embodiments will be omitted.

Based on the type information acquired by the acquisition unit 60, the controller 64 performs control to decrease the compression force after completion of capturing the radiation image to less than the compression force before completion of capturing the radiation image (particularly, a period during which irradiation with the radiation R is performed). Specifically, in a case where the type information indicates that the compression member 40 is of a type having a relatively low strength, the controller 64 may decrease the compression force after completion of capturing the radiation image.

For example, it is assumed that the compression force before completion of capturing the radiation image is 120 N. In a case where the type information indicates a material containing polymethylpentene (PMP) having a relatively low strength, the controller 64 may decrease the compression force after completion of capturing the radiation image, for example, to 80 N or the like, to less than the compression force (120 N) before completion of capturing the radiation image. According to the embodiment described above, the deterioration of the compression member 40 can be appropriately suppressed.

In a case where the compression member 40 is of a type having a relatively high strength, the compression may be continued with the same compression force before and after the capture of the radiation image, but from the viewpoint of reducing the burden on the subject, it is preferable to decrease the compression force after completion of capturing the radiation image. In this case, the controller 64 may make a width of decrease in compression force different before and after completion of capturing the radiation image, depending on the type of the compression member 40. For example, it is assumed that the compression force before completion of capturing the radiation image is uniformly 120 N regardless of the type of the compression member 40. The controller 64 may decrease the compression force after completion of capturing the radiation image to 100 N in a case where the type information indicates a material including PC having a relatively high strength, and decrease the compression force after completion of capturing the radiation image to 80 N in a case where the type information indicates a material including PMP having a relatively low strength.

The release of the compression after acquiring the ultrasound image may be performed by an instruction given from the user via the operation unit 55 of the console 50 and/or the operation unit 26 of the image acquisition device 10, or may be performed by an instruction given from the controller 64 at a point in time at which the ultrasound image is acquired from the image acquisition device 10.

Fourth Embodiment

In a case where the compression member 40 deteriorates, and the compression force is applied to the compression member 40, the compression member 40 may be deformed, and the breast may not be appropriately compressed. Therefore, the console 50 according to the fourth embodiment monitors a deformation state of the compression member 40. Hereinafter, functions of the console 50 according to the fourth embodiment will be described, but a part of the description that overlaps with the first to third embodiments will be omitted.

The acquisition unit 60 acquires the movement amount of the compression member 40 in a state where the breast is compressed in the image acquisition device 10 in the compression direction (vertical direction/Z direction) with respect to the breast. As the movement amount of the compression member 40 in the compression direction, for example, a drive amount from a reference position of the driving unit provided in the compression unit 48 may be used, or a value measured by a sensor that measures a position of the driving unit or the compression member 40 in the compression direction may be used.

As the sensor that measures the position, for example, a device that measures a distance to an imaging target, such as a time-of-flight (TOF) camera, may be used. The TOF camera is a camera that captures a distance image by using a TOF method, irradiates the imaging target with light such as infrared rays, and measures a distance between the TOF camera and the imaging target based on a time until reflected light is received or a phase change between emitted light and the received light. The distance image captured by the TOF camera has distance information representing a distance between the TOF camera and the imaging target for each pixel.

The controller 64 monitors the deformation of the compression member 40 based on the movement amount acquired by the acquisition unit 60. Specifically, the controller 64 may detect that the compression member 40 is deformed in a case where the movement amount is larger than a predetermined threshold value. As the threshold value, for example, for the subject whose breast is compressed at the present time, a previous movement amount in a case where the compression of the breast has been performed in the past may be used. The previous movement amount may be stored, for example, in the storage unit 52.

Figure 12:
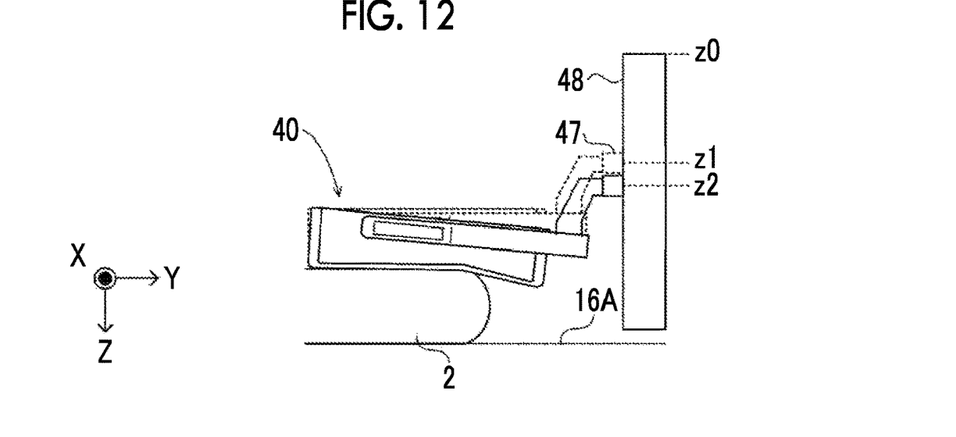
FIG. 12 is a schematic view showing an example of a deformed compression member.

FIG. 12 shows a schematic view of the deformed compression member 40. In FIG. 12, a side of the attachment portion 47 of the compression member 40 is displaced from a position z1 of a non-deformed normal compression member 40 shown by a dotted line to a position z2 in a direction in which the breast is further pushed. In this case, the movement amount of the compression member 40 from the reference position z0 increases. In a case where a difference between the movement amount in the current compression (z0 to z2) and the movement amount in the previous compression (z0 to z1) is larger than a threshold value (for example, ±2 to 3 mm), the controller 64 may detect that the compression member 40 is deformed.

In addition, the controller 64 executes at least one of notification or stopping of the compression by the compression member 40 in a case where the deformation of the compression member 40 is detected. For example, the controller 64 may display the notification content indicating that the compression member 40 may be deformed on the display 54 of the console 50. Further, for example, the controller 64 may perform notification using lighting and/or extinguishing by an LED provided in the console 50 or the image acquisition device 10. Further, for example, the controller 64 may perform notification by emitting a sound from a speaker provided in the console 50 or the image acquisition device 10. According to the embodiment described above, it is possible to prompt the user to confirm the deformation in a case where the compression member 40 may be deformed, so that the breast can be appropriately compressed.

In the fourth embodiment, it has been described that the deformation of the compression member 40 is monitored based on the movement amount, but the present disclosure is not limited thereto. For example, the controller 64 may monitor the deformation of the compression member 40 by using a sensor such as a TOF camera.

In each of the above-described embodiments, it has been described that the image acquisition device 10 reads the identification information provided on the compression member 40, and the acquisition unit 60 acquires the identification information and collates the identification information with the table of FIG. 7, thereby specifying the type information of the compression member 40, but the present disclosure is not limited thereto. For example, the type information may be input by the user via the operation unit 55. Further, for example, the size and shape of the compression member 40 in the type information may be acquired by measurement. As a means for measuring the size and shape of the compression member 40, for example, a device that measures a distance to an imaging target, such as a TOF camera, can be used.

In addition, in each of the above-described embodiments, it has been described that the image acquisition device 10 to be controlled by the console 50 comprises the ultrasound probe 30, but the present disclosure is not limited thereto. For example, as an image acquisition device to be controlled by the console 50, a general mammography device comprising a radiation source, a radiation detector, an imaging table disposed between the radiation source and the radiation detector, and a compression member that compresses the breast between the compression member and the imaging table may be applied. Even in this case, for example, in a case where different types (that is, having different strengths) of the compression members 40 are appropriately interchanged and attached to the mammography device, the console 50 can set the upper limit value of the compression force according to the strength of the compression member 40, so that the deterioration of the compression member 40 can be suppressed.

In addition, in each of the above-described embodiments, it has been described that the console 50 is an example of the control device of the present disclosure, but a device other than the console 50 may have the function of the control device of the present disclosure. In other words, a device other than the console 50, such as the image acquisition device 10 and an external device, may have some or all of the functions of the acquisition unit 60, the setting unit 62, and the controller 64. For example, the controller 20 of the image acquisition device 10 may acquire the type information indicating the type of the compression member 40 and set the upper limit value of the compression force applied to the breast by the compression member 40 based on the type information.

Further, in the above embodiments, for example, as a hardware structure of a processing unit that executes various types of processing such as the controller 20, the acquisition unit 60, the setting unit 62, the controller 64, various types of processors shown below can be used. The various types of processors include, as described above, a CPU which is a general-purpose processor that executes software (program) to function as various types of processing units, as well as a programmable logic device (PLD) which is a processor having a circuit configuration that can be changed after manufacturing such as a field programmable gate array (FPGA), a dedicated electrical circuit which is a processor having a circuit configuration specially designed to execute specific processing such as an application specific integrated circuit (ASIC), and the like.

One processing unit may be configured of one of the various types of processors, or a combination of two or more processors of the same type or different types (for example, a combination of a plurality of FPGAs, or a combination of a CPU and an FPGA). Further, a plurality of processing units may be configured of one processor.

As an example of configuring a plurality of processing units with one processor, first, there is a form in which, as typified by computers such as a client and a server, one processor is configured by combining one or more CPUs and software, and the processor functions as a plurality of processing units. Second, there is a form in which, as typified by a system on chip (SoC) and the like, a processor that implements functions of an entire system including a plurality of processing units with one integrated circuit (IC) chip is used. As described above, the various types of processing units are configured using one or more of the various types of processors as a hardware structure.

Furthermore, as the hardware structure of the various types of processors, more specifically, an electric circuitry in which circuit elements such as semiconductor elements are combined can be used.

In addition, in each of the above-described embodiments, it has been described that various programs in the image acquisition device 10 are stored (installed) in advance in the ROM included in the controller 20, and the information processing program 57 in the console 50 is stored in advance in the storage unit 52, but the present disclosure is not limited thereto. The various programs in the image acquisition device 10 and the information processing program 57 may be provided in a form recorded in a recording medium such as a compact disc read only memory (CD-ROM), a digital versatile disc read only memory (DVD-ROM), and a universal serial bus (USB) memory. In addition, the various programs in the image acquisition device 10 and the information processing program 57 may be provided in a form downloaded from an external device via a network. Furthermore, in addition to the program, the technique of the present disclosure extends to a storage medium that non-transitorily stores the program.

The technique of the present disclosure can also appropriately combine the above-described embodiments and examples. The above-described contents and illustrated contents are detailed descriptions of parts related to the technique of the present disclosure, and are merely examples of the technique of the present disclosure. For example, the above descriptions related to configurations, functions, operations, and effects are descriptions related to examples of configurations, functions, operations, and effects of the parts related to the technique of the present disclosure. Therefore, it is needless to say that unnecessary parts may be deleted, or new elements may be added or replaced with respect to the above-described contents and illustrated contents within a scope not departing from the spirit of the technique of the present disclosure.

What is claimed is:

1. A control device comprising at least one processor, wherein the at least one processor is configured to:
   acquire type information indicating a type of a compression member attached to an image acquisition device that captures a radiation image by irradiating a breast in a compressed state between an imaging table and the compression member with radiation; and
   set an upper limit value of a compression force applied to the breast by the compression member based on the type information.

2. The control device according to claim 1, wherein the type information indicates at least one of a material, a size, or a shape of the compression member.

3. The control device according to claim 2, wherein the type information indicates at least the material of the compression member.

4. The control device according to claim 2, wherein the at least one processor is configured to:
   in a case where the type information indicates that the compression member is of a type having a relatively high strength, set a relatively high value as the upper limit value; and
   in a case where the type information indicates that the compression member is of a type having a relatively low strength, set a relatively low value as the upper limit value.

5. The control device according to claim 4, wherein the at least one processor is configured to, in a case where the type information indicates a material containing polymethylpentene, set a value relatively lower than those of other materials as the upper limit value.

6. The control device according to claim 1, wherein the at least one processor is configured to acquire, for each compression member, a log including usage information indicating at least one of the compression force, a compression time, or the number of times of compression applied to the breast by the compression member, or an elapsed time from a point in time at which the compression member is first used.

7. The control device according to claim 6, wherein the processor is configured to, in a case where the usage information satisfies a condition predetermined for each type of the compression member, issue a notification.

8. The control device according to claim 6, wherein the at least one processor is configured to:
   derive a load amount of the compression member based on the usage information; and
   in a case where the load amount satisfies a condition predetermined for each type of the compression member, issue a notification.

9. The control device according to claim 6, wherein the at least one processor is configured to, in a case where the usage information satisfies a condition predetermined for each type of the compression member, set a relatively low value as the upper limit value.

10. The control device according to claim 6, wherein the at least one processor is configured to:
    derive a load amount of the compression member based on the usage information; and
    in a case where the load amount satisfies a condition predetermined for each type of the compression member, set a relatively low value as the upper limit value.

11. The control device according to claim 1, wherein the at least one processor is configured to decrease the compression force after completion of capturing the radiation image to less than the compression force before completion of capturing the radiation image, based on the type information.

12. The control device according to claim 11, wherein the processor is configured to, in a case where the type information indicates a material containing polymethylpentene, decrease the compression force after completion of capturing the radiation image to less than the compression force before completion of capturing the radiation image.

13. The control device according to claim 1, wherein the at least one processor is configured to:
    acquire a movement amount of the compression member in a compression direction with respect to the breast;
    monitor deformation of the compression member based on the movement amount; and
    in a case where the deformation of the compression member is detected, execute at least one of notification or stopping of compression by the compression member.

14. The control device according to claim 13, wherein the at least one processor is configured to, in a case where the movement amount becomes larger than a predetermined threshold value, detect that the compression member is deformed.

15. An image acquisition device comprising:
    the control device according to claim 1;
    a radiation source;
    a radiation detector;
    an imaging table disposed between the radiation source and the radiation detector; and
    a compression member that compresses a breast between the compression member and the imaging table.

16. The image acquisition device according to claim 15, further comprising an ultrasound probe disposed between the radiation source and the compression member.

17. A control method comprising:
    acquiring type information indicating a type of a compression member attached to an image acquisition device that captures a radiation image by irradiating a breast in a compressed state between an imaging table and the compression member with radiation; and
    setting an upper limit value of a compression force applied to the breast by the compression member based on the type information.

18. A non-transitory computer-readable storage medium storing a control program for causing a computer to execute a process comprising:

acquiring type information indicating a type of a compression member attached to an image acquisition device that captures a radiation image by irradiating a breast in a compressed state between an imaging table and the compression member with radiation; and setting an upper limit value of a compression force applied to the breast by the compression member based on the type information.

* * * * *